US008766412B2

(12) United States Patent
Matsumoto

(10) Patent No.: US 8,766,412 B2
(45) Date of Patent: Jul. 1, 2014

(54) SEMICONDUCTOR DEVICE, METHOD OF MANUFACTURING THE SAME, AND SILANE COUPLING AGENT

(75) Inventor: Manabu Matsumoto, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1018 days.

(21) Appl. No.: 12/725,940

(22) Filed: Mar. 17, 2010

(65) Prior Publication Data
US 2010/0270659 A1    Oct. 28, 2010

(30) Foreign Application Priority Data

Apr. 23, 2009   (JP) ................................ 2009-105457

(51) Int. Cl.
*H01L 23/58*    (2006.01)
(52) U.S. Cl.
USPC ..... 257/651; 257/629; 257/632; 257/E23.002
(58) Field of Classification Search
USPC ......... 438/460, 692, 759, 778, 781, 789, 790, 438/794; 257/434, 651, 784, 689, 666, 40, 257/632, 759, 760, 756, 643, 645, 621, 257/E23.01, E31.11, E23.07, 642; 430/234; 427/258, 427.1; 428/624
See application file for complete search history.

(56) References Cited

U.S. PATENT DOCUMENTS

| 5,536,573 | A   | * | 7/1996  | Rubner et al. ............... 428/378 |
| 7,633,129 | B1  | * | 12/2009 | Shi et al. ................... 257/400 |
| 8,426,880 | B2  | * | 4/2013  | Song et al. .................. 257/98 |
| 2002/0041027 | A1 | * | 4/2002 | Sugizaki ...................... 257/737 |
| 2005/0110397 | A1 | * | 5/2005 | Masuda ........................ 313/504 |
| 2006/0234151 | A1 | * | 10/2006 | Nakagawa et al. ........... 430/234 |
| 2007/0035036 | A1 | * | 2/2007 | Sota et al. .................... 257/784 |
| 2009/0008732 | A1 | * | 1/2009 | Kojima ......................... 257/434 |
| 2009/0191667 | A1 |   | 7/2009 | Higashino et al. |
| 2009/0252944 | A1 | * | 10/2009 | Kurita et al. .................. 428/220 |
| 2009/0309205 | A1 | * | 12/2009 | Takahashi ..................... 257/686 |

FOREIGN PATENT DOCUMENTS

| JP | A-H04-211142   | 8/1992  |
| JP | A-2002-501307  | 1/2002  |
| JP | A-2004-214612  | 7/2004  |
| JP | A-2005-302871  | 10/2005 |
| JP | A-2007-048958  | 2/2007  |
| JP | A-2009-158739  | 7/2009  |

OTHER PUBLICATIONS

Background Art Information Sheet provided by applicant (Dec. 7, 2009) (1 page total).
Y. Honma et al. "Introduction to Chemistry and Materials Science for Nanotechnology, Ver.1: Chapter 5: Bottom up Construction" The Surface Science Society of Japan, 2007: 115-118 (English translation enclosed).
Office Action mailed Jun. 5, 2012 in corresponding JP Application No. 2009-105457 (and English translation).

* cited by examiner

*Primary Examiner* — Leonard Chang
(74) *Attorney, Agent, or Firm* — Posz Law Group, PLC

(57) ABSTRACT

A semiconductor chip has devices formed on a first principal plane of a semiconductor substrate, wherein a second principal plane of the semiconductor substrate is planarized, and an organic film having plus charges on an outer side is provided on the second principal plane.

20 Claims, 5 Drawing Sheets

|  | #2,000 | #8,000 | DRY POLISH | CMP |
|---|---|---|---|---|
| REAR SURFACE ROUGHNESS (Ra) [nm] | 18.15 | 10.89 | 0.30 | 0.54 |
| DEFLECTIVE STRENGTH [N] | 1.20 | 2.44 | 3.49 | 3.37 |

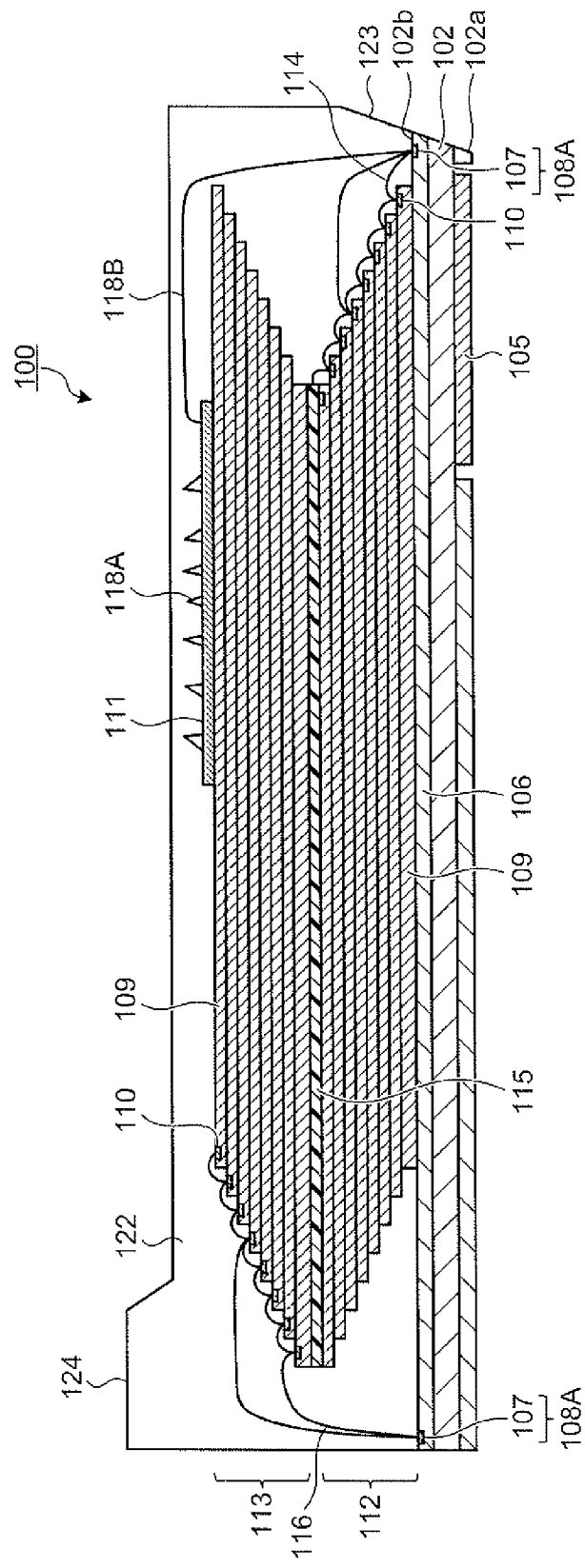

SEMICONDUCTOR DEVICE, METHOD OF MANUFACTURING THE SAME, AND SILANE COUPLING AGENT

CROSS-REFERENCE TO RELATED APPLICATIONS

This application is based upon and claims the benefit of priority from the prior Japanese Patent Application No. 2009-105457, filed on Apr. 23, 2009; the entire contents of which are incorporated herein by reference.

BACKGROUND OF THE INVENTION

1. Field of the Invention

The present invention relates to a semiconductor device, a method of manufacturing the same, and a silane coupling agent.

2. Description of the Related Art

In a structure proposed for a semiconductor device such as a NAND flash memory, although external dimensions are the same as those in the past, a storage capacity larger than that in the past is provided by laminating a plurality of memory chips on a wiring substrate stepwise and sealing the memory chips with resin (see, for example, Japanese Patent Application Laid-Open No. 2005-302871). To further increase the storage capacity in such a semiconductor device, it is necessary to increase the number of lamination steps of the memory chips. However, because there is a limit in the external dimensions, in particular, thickness of the semiconductor device, the thickness of the memory chips has to be reduced. Therefore, in recent years, thin-layering of semiconductor chips such as memory chips is advanced and the thickness of a wafer is reduced to be smaller than 100 micrometers. Usually, on the rear surface of the wafer, a fractured layer having unevenness is formed to suppress diffusion of ionic impurities from the rear surface to the inside of the wafer in a manufacturing process for a semiconductor device. However, when the thickness of the wafer is smaller than 100 micrometers, a deficiency tends to occur in that deflective strength of the chips falls and the chips are broken by pressure in mounting the chips. Therefore, the rear surface of the wafer (the chips) is planarized by polishing processing such as the chemical mechanical polishing (CMP) method or the etching method (see, for example, Japanese Patent Application Laid-Open No. 2007-48958).

However, when the rear surface of the wafer (the chips) is planarized by the polishing processing, the ionic impurities diffuse from the rear surface to the inside of the wafer as explained above. To cope with the problem, Japanese Patent Application Laid-Open No. 2007-48958 discloses that the fractured layer is left on the rear surface even in the case of the wafer having thickness smaller than 100 micrometers. However, in this case, the deflective strength of the wafer (the chips) falls because of the presence of the fractured layer. When the thickness of the wafer is smaller than 100 micrometers in this way, it is difficult to simultaneously attain the suppression of the diffusion of the ionic impurities to the inside of the wafer and the suppression of the fall in the deflective strength with the method in the past.

BRIEF SUMMARY OF THE INVENTION

A semiconductor chip has devices formed on a first principal plane of a semiconductor substrate according to an embodiment of the present invention, wherein a second principal plane of the semiconductor substrate is planarized, and an organic film having plus charges on an outer side is provided on the second principal plane.

A method of manufacturing a semiconductor device according to an embodiment of the present invention comprises: polishing, using a CMP method or a dry polish method, a second principal plane of a semiconductor substrate having devices formed on a first principal surface; cleaning the second principal plane with an oxidizing agent to form an OH group on a surface of the second principal plane; and modifying the second principal plane of the semiconductor substrate with a silane coupling agent to form an organic film having plus charges on an outer side.

A silane coupling agent according to an embodiment of the present invention forms, according to a hydrolysis reaction and a condensation reaction, covalent binding between the silane coupling agent and a front surface of a semiconductor substrate on which an OH group is formed and modifies the front surface of the semiconductor substrate to form an organic film such that a functional group having plus charges is arranged on a side not in contact with the semiconductor substrate.

BRIEF DESCRIPTION OF THE DRAWINGS

FIG. 7 is a sectional view taken along A-A in FIG. 6.

DETAILED DESCRIPTION OF THE INVENTION

Exemplary embodiments of the present invention are explained in detail below with reference to the accompanying drawings. The present invention is not limited by the embodiments. Sectional views of semiconductor devices referred to below are schematic. A relation between the thickness and the width of a layer, a ratio of the thicknesses of layers, and the like are different from actual ones. The thicknesses described below are examples only and the thicknesses of the layers are not limited to these thicknesses.

Figure 1:
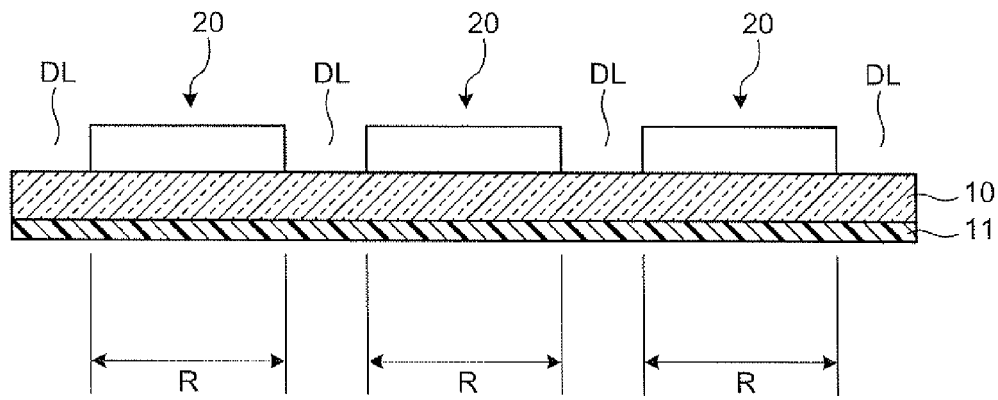
FIG. 1 is a schematic sectional view of the configuration of a semiconductor device according to a first embodiment of the present invention.

FIG. 1 is a schematic sectional view of the configuration of a semiconductor device according to a first embodiment of the present invention. A plurality of device formation regions R to be divided later are provided on a first principal plane (hereinafter, "front surface") of a semiconductor substrate (a wafer) 10 such as a silicon substrate. In the respective device formation regions R, chips 20 as semiconductor devices including elements such as field effect transistors and wires are formed. Examples of the chips 20 include a memory chip on which a storage device such as a NAND flash memory is formed and a controller chip on which a device for controlling the memory chip. Among the device formation regions R (the chips 20) adjacent to one another, dicing lines DL for dividing the chips 20 are formed.

A second principal plane (hereinafter, "rear surface") of the semiconductor substrate 10 is planarized with a fractured layer removed therefrom. It is desirable that the rear surface is planarized to have deflective strength enough for preventing the chips 20 from being broken when the chips 20 are mounted. As a result of an experiment, it is desirable that, for example, when the thickness of the semiconductor substrate 10 is 55 micrometers, the deflective strength is equal to or larger than 3 N. Arithmetic mean roughness Ra of the rear surface of the semiconductor substrate 10 in this case is equal to or smaller than 1 nanometer.

On the planarized rear surface, a rear-surface treatment film 11 formed of an organic thin film having a barrier function against ionic impurities is formed. Specifically, the rear surface of the semiconductor substrate 10 has a structure modified with a silane coupling agent. A functional group having plus charges is arranged on the front surface side (the outer side) of the rear-surface treatment film 11 modified with the silane coupling agent. It is desirable that the rear-surface treatment film 11 is a self-organizing monomolecular film.

In this way, the rear-surface treatment film 11 in which the functional group having the plus charges on the outer side thereof is formed on the planarized rear surface of the semiconductor substrate 10. Therefore, it is possible to increase the deflective strength of the semiconductor substrate (the wafer or the chips) 10 compared with the deflective strength of the semiconductor substrate 10 having the fractured layer. The semiconductor substrate 10 has a barrier effect for preventing new intrusion of the ionic impurities (movable ions) having the plus charges from the rear surface.

Figure 2:
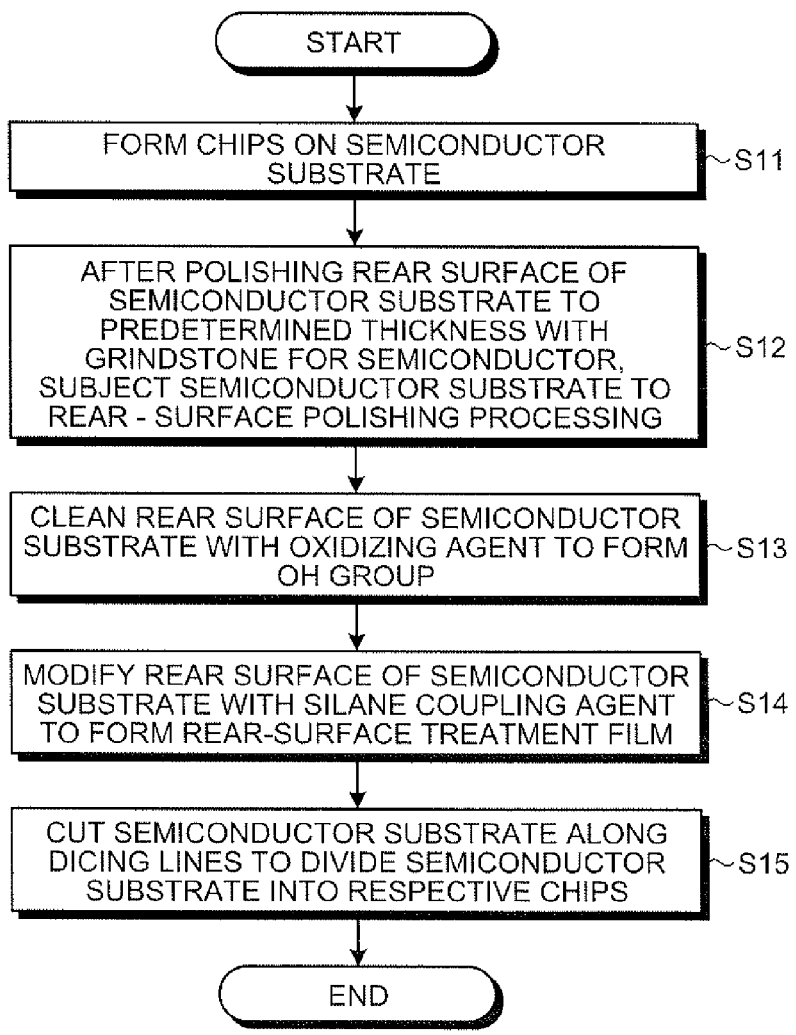
FIG. 2 is a flowchart for explaining an example of a procedure of a method of manufacturing a semiconductor device according to the first embodiment.
Figure 3A:
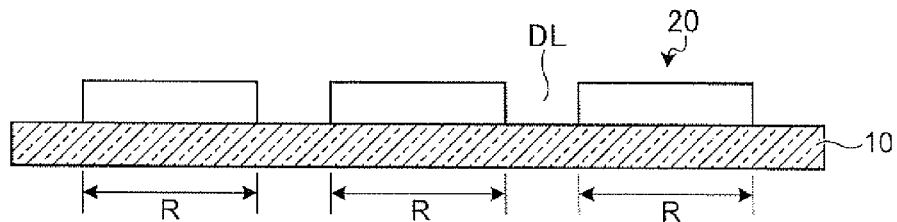
FIGS. 3A to 3E are schematic sectional views of the example of the method of manufacturing a semiconductor device according to the first embodiment.

FIG. 2 is a flowchart for explaining an example of a procedure of a method of manufacturing a semiconductor device according to the first embodiment. FIGS. 3A to 3E are schematic sectional views of the example of the procedure of the method of manufacturing a semiconductor device according to the first embodiment. First, as shown in FIG. 3A, devices such as field effect transistors, wires, and the like are formed on the device formation regions R on the front surface side of the semiconductor substrate 10 by a publicly-known method including a film formation process, an impurity introduction process, a photolithography process, an etching process, a metallization process, and inspection processes among the processes to form the chips 20 (step S11). The dicing lines DL are formed among the device formation regions R. The dicing lines DL are used in cutting the semiconductor substrate 10 into the respective chips 20 in a dicing process explained later.

Figure 3B:

Subsequently, the thickness of the semiconductor substrate 10 is measured. Then, as shown in FIG. 3B, after polishing the semiconductor substrate 10 to predetermined thickness by using a coarse grindstone, the semiconductor substrate 10 is subjected to rear-surface polishing processing to reduce the roughness of the rear surface to be equal to or smaller than a predetermined value (step S12). Examples of a method for the rear-surface polishing processing include polishing methods that can perform planarization at an atom level unit such as the CMP method and the dry polish method.

Figure 3C:
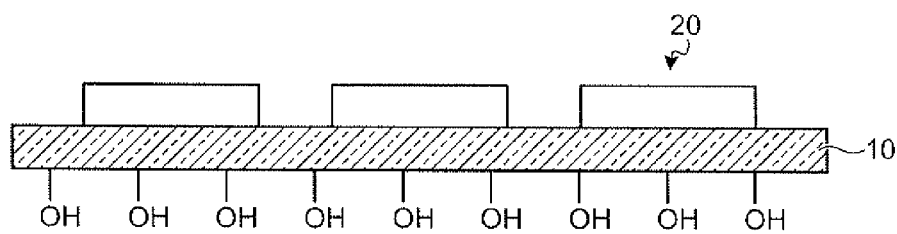

Thereafter, as shown in FIG. 3C, the semiconductor substrate 10, the rear surface of which is polished, is cleaned by using an oxidizing agent. As the oxidizing agent, for example, a heated solution as a mixture of hydrogen peroxide (31%) and concentrated sulfuric acid can be used. Consequently, the rear surface of the semiconductor substrate 10 is cleaned and an OH group is formed on the front surface of the semiconductor substrate (step S13).

Figure 3D:
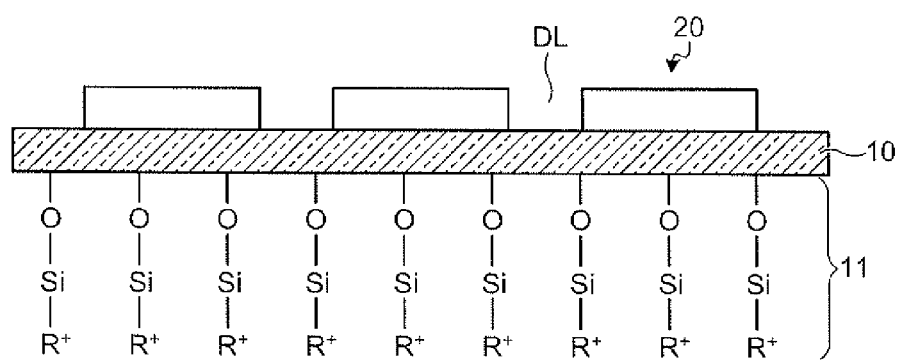
Figure 3E:
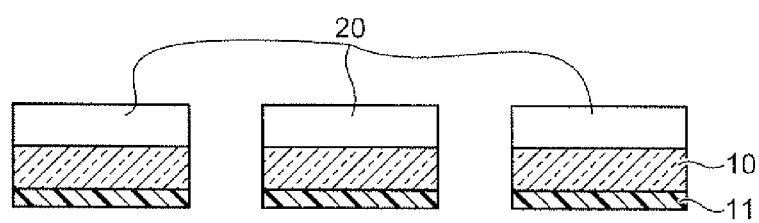

Thereafter, as shown in FIG. 3D, the rear surface of the semiconductor substrate 10 on which the OH group is formed is modified with the silane coupling agent to form the rear-surface treatment film 11 in a state in which water vapor is not present (step S14). For example, the semiconductor substrate 10 having the OH group on the rear surface is immersed for a predetermined time (e.g., five minutes) in a solution in which the silane coupling agent, a functional group at the end of which has plus charges, is dissolved in an organic solvent at density of about 5%. Consequently, the silane coupling agent combines with the rear surface of the semiconductor substrate 10 via the OH group according to a hydrolysis reaction and a condensation reaction. Further, moisture is removed to form covalent binding between the silane coupling agent and the rear surface of the semiconductor substrate 10. The rear surface of the semiconductor substrate 10 is modified with the silane coupling agent and the rear-surface treatment film 11 formed of an organic thin film is formed. In the rear-surface treatment film 11, the functional group at the end having the plus charges is arranged on the outer side.

As such a silane coupling agent, a silane coupling agent having a functional group with plus charges such as an amino group is desirable. Specifically, examples of the silane coupling agent include hydrochloride groups of 3-aminopropyl-trimethoxysilane (hereinafter, "3-APMS"), 3-aminopropyl-trietoxysilane, N-2-(aminoethyl)-3-aminopropylmethyldimethoxysilane, N-2-(aminoethyl)-3-aminopropyltrimethoxysilane, N-2-(aminoethyl)-3-aminopropyltriethoxysilane, 3-triethoxysilyl-N-(1,3-dimethyl-butylidene) propylamine, N-phenyl-3-aminopropyltrimethoxysilane, and N-(vinylbenzyl)-2-aminoethyl-3-aminopropyltrimethoxysilane.

When the overall thickness of the chip 20 is taken into account, the silane coupling agent is desirably a silane coupling agent that forms a self-organizing monomolecular film. Therefore, the self-organizing monomolecular film can be formed by, after the rear surface of the semiconductor substrate 10 is immersed in the silane coupling agent (e.g., 3-APMS) solution, cleaning the rear surface of the semiconductor substrate 10 with ultrapure water to remove excess 3-APMS.

Thereafter, as shown in FIG. 35, the semiconductor substrate (the wafer) 10 is cut along the dicing lines DL to divide the chips 20 (step S15). Consequently, the semiconductor device according to the first embodiment is obtained.

At step S14, the rear surface of the semiconductor substrate 10 can be modified with the silane coupling agent according to other methods. For example, the rear-surface treatment film 11 can be formed on the rear surface of the semiconductor substrate 10 under a decompressed atmosphere. The silane coupling agent can be applied to the rear surface of the semiconductor substrate 10 according to the application method to form the rear-surface treatment film 11.

As a method of forming the rear-surface treatment film 11 under the decompressed atmosphere, for example, the semiconductor substrate 10 after being cleaned by the oxidizing agent is put in a decompressable container, the silane coupling agent such as the 3-APMS solution is injected into the container under the decompressed atmosphere, and the semiconductor substrate 10 is left untouched for eight hours. Consequently, the rear surface of the semiconductor substrate 10 is modified with the silane coupling agent and the rear-surface treatment film 11 is formed on the rear surface of the semiconductor substrate 10.

In the method of forming the rear-surface treatment film 11 according to the application method, for example, the silane coupling agent such as the 3-APMS solution is applied over the entire rear surface of the semiconductor substrate 10 according to the application method such as the spin coating method. Consequently, the rear surface of the semiconductor substrate 10 is modified with the silane coupling agent and the rear-surface treatment film 11 is formed on the rear surface of the semiconductor substrate 10.

In the above explanation, at step S15, the chips 20 are divided into the respective chips 20 along the dicing lines DL. However, this chip dividing processing can be performed before the polishing processing for the rear surface of the semiconductor substrate 10 at step S12. In this case, the processing at steps S12 to S14 is applied to the divided respective chips 20. Consequently, there is an effect that it is possible to form rear-surface treatment films 11 only on the chips 20 in use and it is possible to reduce an amount of the silane coupling agent in use.

Figures 4, 5:
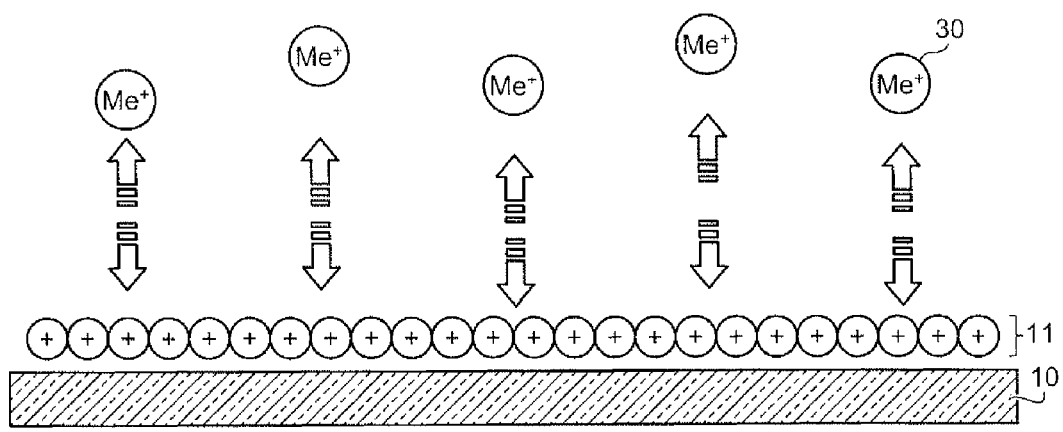
FIG. 4 is a schematic sectional view for explaining an effect of the semiconductor device according to the first embodiment.
FIG. 5 is a diagram for explaining a relation between a polished state and deflective strength of the rear surface of a semiconductor substrate.

FIG. 4 is a schematic sectional view for explaining an effect of the semiconductor device according to the first embodiment. As shown in FIG. 4, the rear-surface treatment film 11, the end on the outer side of which not on the substrate side includes the functional group having plus charges, is formed on the rear surface of the silicon substrate as the semiconductor substrate 10. In this way, the rear surface of the silicon substrate is charged in plus. Therefore, in a process after the formation of the rear-surface treatment film 11 (e.g., a process for mounting on a wiring substrate), even if ionic impurities (movable ions) 30 such as copper ions or sodium ions having plus charges approach the rear surface of the silicon substrate, intrusion of the ionic impurities 30 into the rear surface of the silicon substrate is suppressed by the Coulomb repulsion.

FIG. 5 is a diagram for explaining a relation between a polished state and deflective strength of the rear surface of a semiconductor substrate. In FIG. 5, arithmetic mean roughness Ra and deflective strength of the rear surface are shown concerning semiconductor substrates polished by using grindstones #2,000 and #8,000, a semiconductor substrate polished by the dry polish method, and a semiconductor substrate polished by the CMP method in rear-surface polishing processing.

The arithmetic mean roughnesses Ra of the rear surfaces of the semiconductor substrates polished by using the grindstones #2,000 and #8,000 are respectively 18.15 nanometers and 10.89 nanometers. The arithmetic means roughnesses Ra of the rear surfaces of the semiconductor substrates polished by the dry polish method and the CMP method are respectively 0.30 nanometers and 0.54 nanometers. The roughnesses of the rear surfaces of the semiconductor devices are completely different. This is also evident from the fact that, although not shown in the figure, looking at sectional transmission electron microscope (TEM) images and atomic force microscope (AFM) images obtained as a result of performing an observation, whereas the latter two rear surfaces are flat at an atomic layer level, unevenness is larger in the former two rear surfaces compared with the latter two rear surfaces. As a result, the chip deflective strength is higher in the rear surfaces of the semiconductor substrates polished by the dry polish method and the CMP method compared with the rear surfaces of the semiconductor substrates polished by the coarse grindstones #2,000 and #8,000.

As indicated by this result, it is desirable that a semiconductor substrate has a rear surface having the arithmetic mean roughness Ra that realizes the chip deflective strength equal to or higher than about 3 N. According to this result, it is desirable that the arithmetic mean roughness Ra is equal to or smaller than about 1 nanometer. It is possible to prevent intrusion of ionic impurities into the semiconductor substrate 10 by forming the rear-surface treatment film 11 formed of the organic film, the outer side of which is charged in plus, on the rear surface of the semiconductor substrate 10 planarized by the rear-surface polishing processing method such as the dry polish method or the CMP method.

According to the first embodiment, the planarized rear surface of the semiconductor substrate 10 is cleaned by the oxidizing agent to form the OH group and the rear surface of the semiconductor film 10 is modified with the silane coupling agent having the functional group charged in plus at the end to form the rear-surface treatment film 11 having the plus charges on the outer side. This makes it possible to prevent new intrusion of metal ions diffused, for example, during etching in a pre-process into the rear surface of the semiconductor substrate 10. In other words, there is an effect that it is possible to prevent intrusion of movable ions such as Cu ions and Na ions while increasing the deflective strength compared with the deflective strength of the semiconductor substrate 10 having the fractured layer on the rear surface and suppressing warp of the chips 20.

Because the rear-surface treatment film 11 is formed of the organic film, it is possible to inexpensively and easily realize a barrier effect against movable metal ions. In particular, because the rear-surface treatment film 11 is the self-organizing monomolecular film, it is possible to modify the rear surface of the semiconductor substrate 10 by the monomolecular film of several nanometers. The thickness of the chips 20 is not affected.

Figure 6:
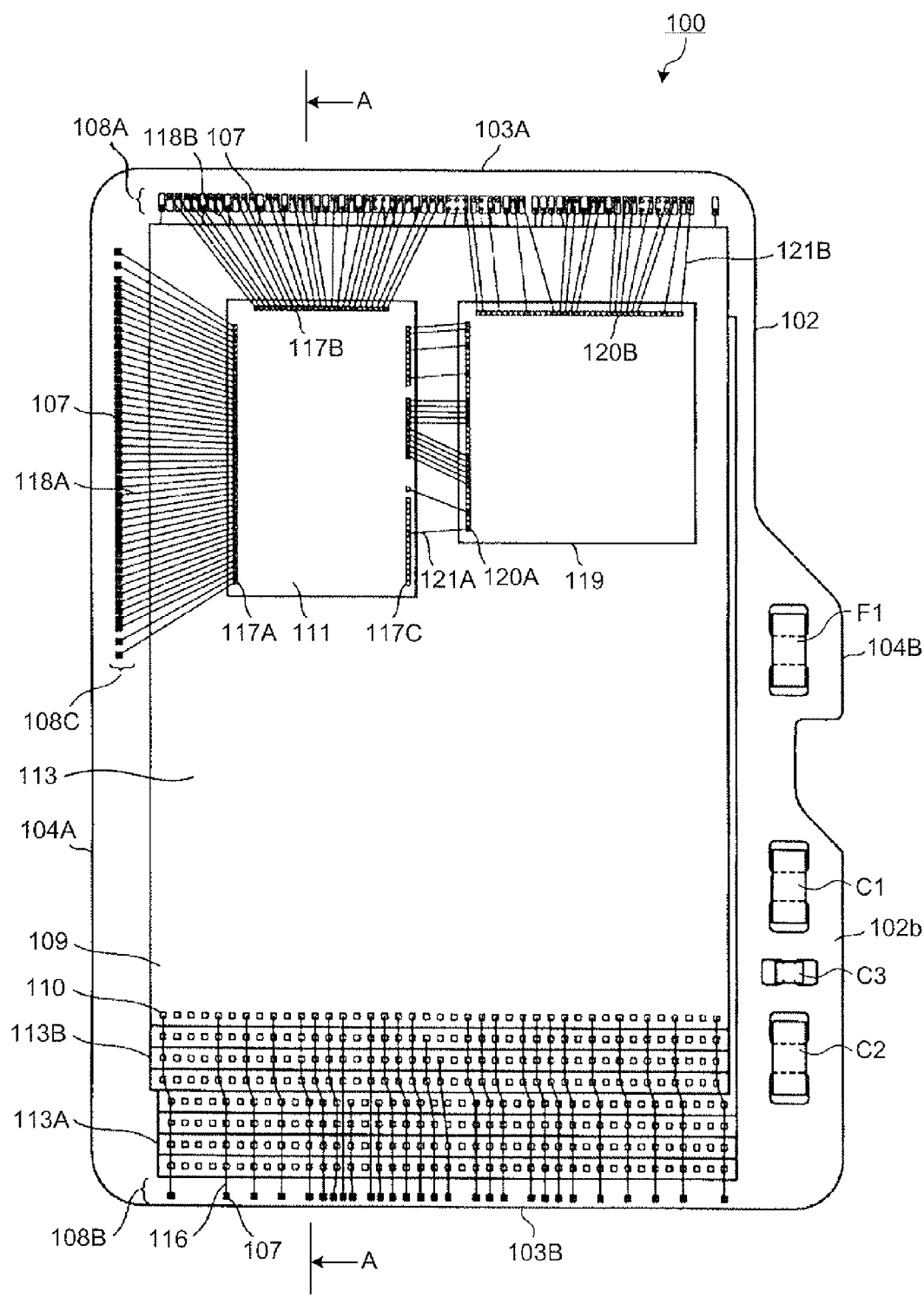
FIG. 6 is a schematic plan view of an example of the configuration of a semiconductor device according to a second embodiment of the present invention.

FIG. 6 is a schematic plan view of an example of the configuration of a semiconductor device according to a second embodiment of the present invention. FIG. 7 is a sectional view taken along A-A in FIG. 6. A semiconductor memory card such as a micro SD card is an example of the semiconductor device shown in the figures.

The semiconductor device 100 includes a wiring substrate 102 that functions as both a device mounting substrate and a termination formation substrate. The wiring substrate 102 is formed by, for example, providing a wiring network in the inside and the surface of an insulative resin substrate. Specifically, a printed wiring board made of glass-epoxy resin or bismaleimide-triazine resin (BT resin) is applied as the wringing board 102. An external shape of the wiring substrate 102 is a substantially rectangular shape. One short side 103A of the wiring substrate 102 corresponds to the leading end of the semiconductor memory card inserted into a card slot and the other short side 103B corresponds to the trailing end of the semiconductor memory card. Whereas one long side 104A of the wiring substrate 102 has a linear shape, the other long side 104B has a cutout and a narrowed section indicating directions of the front and the rear and the front side and the back side of the semiconductor memory card. Corners of the wiring substrate 102 are formed in a curved shape (an R shape).

On the short side 103A side of a first principal plane 102a as the terminal formation surface of the wiring substrate 102, an external connection terminal 105 made of a metal layer as an input and output terminal of the semiconductor memory card is formed. On the first principal plane 102a of the wiring substrate 102, a first wiring network (not shown) is provided in an area excluding a formation area of the external connection terminal 105. The first wiring network is covered with an insulative layer (not shown) made of an insulative adhesive seal, an adhesive tape, or the like.

A second principal plane 102b as the device mounting surface of the wiring substrate 102 includes a chip mounting section 106 and a second wiring network including connection pads 107. The second wiring network including the connection pads 107 is electrically connected to the external connection terminal 105 and the first wiring network via not-shown internal wiring (through hole, etc.) of the wiring substrate 102. The connection pads 107 are respectively arranged in a first pad area 108A along the short side 103A, a second pad area 108B along the short side 103B, and a third pad area 108C along the long side 104A.

In the chip mounting section 106 of the wiring substrate 102, a plurality of memory chips (semiconductor chips) 109 such as a NAND flash memory are laminated and mounted. The memory chips 109 have the same rectangular shape. The memory chips 109 have short-one-side pad structures respectively including electrode pads 110 arrayed along one side of the external shape, specifically, one short side.

On the memory chip 109 at the top step (a sixteenth step), a controller chip (a semiconductor chip) 111 and a relay chip (a semiconductor chip) 119 are arranged. The controller chip 111 selects, out of the memory chips 109, the memory chip 109 to which data is written and from which data is read out and performs writing of data in the selected memory chip 109 and readout of data stored in the selected memory chip 109. Electrode pads 117A to 117C are formed in a C shape on the upper surface of the controller chip 111. The electrode pad 117A arrayed along a first external shape side and the connection pad 107 in the third pad area 1080 of the wiring board 102 are electrically connected by a metal wire 118A such as an Au wire. The electrode pad 117B arrayed along a second external shape side and the connection pad 107 in the second pad area 108B of the wiring board 102 are electrically connected by a metal wire 1081 such as an Au wire.

The relay chip 119 is arranged adjacent to a third external shape side of the controller chip 111. On the upper surface of the relay chip 119, electrode pads (relay pads) 120A and 120B respectively arrayed along one external shape side and another external shape side orthogonal to the one external shape side are formed. The electrode pad 120A is arranged to be opposed to the electrode pad 117C arrayed along the third external shape side of the controller chip 111 and is connected to the electrode pad 1170 via a metal wire for relay 121A. The electrode pad 120B is arranged to be located near the first pad area 108A of the wiring substrate 102 and is connected to the connection pad 107 via a metal wire for relay 1213. In this way, the relay chip 119 electrically connects the electrode pad 1170 of the controller chip 111 and the connection pad 117 arranged in the first pad area 108A.

The memory chips 109 are divided into first and second memory chip groups 112 and 113 (semiconductor chip groups). Each of the memory chip groups 112 and 113 includes eight memory chips 109. The eight memory chips 109 included in the first memory chip group 112 are laminated stepwise in order on the chip mounting section 106. The eight memory chips 109 included in the second memory chip group 113 are laminated stepwise in order on the first memory chip group 112. A step direction of the second memory chip group 113 (a direction toward the upper steps of the memory chips 109 laminated stepwise) is set in a direction opposite to a step direction of the first memory chip group 112.

Among the eight memory chips 109 included in the first memory chip group 112, the memory chip 109 at the bottom step (a first step) is bonded on the chip mounting section 106 of the wiring substrate 102 via an adhesive layer (not shown) with an electrode formation surface having the electrode pad 110 directed upward. As the bonding layers, a general die attach film (adhesive film) containing polyimide resin, epoxy resin, acryl resin, or the like as a main component is used. The same holds true for an adhesive layer of the other memory chips 109 included in the first memory chip group 112. The memory chip 109 at the first step is arranged with a pad array side thereof directed to the short side 103A of the wiring board 102. Specifically, the memory chip 109 is arranged such that the electrode pad 110 is located near the first pad area 108A of the wiring substrate 102.

The memory chip 109 at the second step is bonded on the memory chip 109 at the first step via a bonding layer (not shown) with an electrode formation surface having the electrode pad 110 directed upward while exposing the electrode pad 110 of the memory chip 109 at the first step. Similarly, the remaining six memory chips (memory chips at the third to eighth steps) are respectively bonded in order via adhesive layers (not shown) with positions of short sides thereof shifted in the direction of long sides such that the electrode pads 110 of the memory chips 109 on lower step sides are exposed. In this way, the eight memory chips (the memory chips at the first to eight steps) included in the first memory chip group 112 are laminated stepwise with positions of short sides thereof shifted along the long side direction with pad array sides of the memory chips directed in the same direction (the direction of the short side 103A) and such that the electrode pads 110 of the memory chips 109 on the lower step sides are exposed.

The first memory chip group 112 has the stepwise laminated structure. Therefore, all the electrode pads 110 of the memory chips 109 included in the first memory chip group 112 are located near the first pad area 108A while being exposed upward. The electrode pads 110 of the eight memory chips 109 included in the first memory chip group 112 are respectively electrically connected, via the first metal wire (an Au wire, etc.) 114, to the connection pad 107 arranged in the first pad area 108A.

Among the eight memory chips 109 included in the second memory chip group 113, the memory chip 109 at the bottom step (the ninth step) is bonded to, with an electrode formation surface having the electrode pad 110 directed upward, the memory chip 109 at the top step (the eighth step) in the first memory chip group 112 via the insulative adhesive layer 115, which functions as a spacer layer, such that short sides and long sides of the memory chips 109 respectively overlap each other. Specifically, the electrode pad 110 of the memory chip 110 at the eighth step is not exposed in plan view and is closed by the memory chip 109 at the ninth step. Therefore, the insulative adhesive layer 115 softens or melts at least in a part thereof at temperature during bonding and bonds the memory chip 109 at the eight step and the memory chip 109 at the ninth step while drawing an end (a chip side end) of the first metal wire 114 connected to the memory chip 108 at the eight step into the inside thereof. An adhesive made of insulative resin is used as the insulative adhesive layer 115 to secure insulation of the first metal wire 114.

The memory chip 109 at the bottom step (the ninth step) in the second memory chip group 113 is arranged with a pad array side thereof directed to the short side 103B of the wiring substrate 102. Specifically, the memory chips 109 included in the second memory chip group 113 are arranged with pad array sides thereof directed in a direction opposite to the direction of the first memory chip group 112. Consequently, the electrode pads 110 of the memory chips 109 included in the second memory chip group 113 are located near the second pad area 108B on the opposite side of the first pad area 108A connected to the first memory chip group 112.

The memory chip 109 at the tenth step is bonded on the memory chip 109 at the ninth step via an adhesive layer (not shown) with an electrode formation surface having the electrode pad 110 directed upward while exposing the electrode pad 110 of the memory chip 109 at the ninth step. The memory chip 109 at the tenth step is arranged with a pad array side thereof directed in a direction same as that of the memory chip 109 at the ninth step. Similarly, the remaining six memory chips (memory chips at the eleventh to sixteenth steps) of the second memory chip group 113 are respectively bonded stepwise in a direction opposite to the step direction of the first memory chip group 112 in order via adhesive layers (not shown) with pad array sides thereof directed in the direction same as that of the memory chip 109 at the ninth step and with positions of short sides thereof shifted along the long side direction such that the electrode pads 110 of the memory chips on the lower step sides are exposed. Like the adhesive layers used in the first memory chip group 112, as the bonding layers of the memory chips 109 at the tenth to sixteenth steps, the general die attach film (adhesive film) is used.

The second memory chip group 113 has the stepwise laminated structure. Therefore, all the electrode pads 110 of the memory chips 109 included in the second memory chip group 113 are located near the second pad area 108B while being exposed upward. The electrode pads 110 of the eight memory chips 109 included in the second memory chip group 113 are respectively electrically connected, via the second metal wire (an Au wire, etc.) 116, to the connection pad 107 arranged in the second pad area 108B.

The thickness of the memory chips 109 included in the first memory chip group 112 is not always limited. However, it is desirable to set the thickness of the memory chip 109 at the bottom step (the first step) larger than the thickness of the other memory chips 109 (the second to eighth steps). This is because, since the memory chip 109 at the first step is arranged on an uneven section (an uneven section due to a step caused by presence or absence of a wiring layer, a step caused by a through hole section, a step caused by a terminal and a test pad, and the like) present on the surface of the wiring substrate 102, if the thickness of the memory chip 109 at the first step is set too small, it is likely that a crack occurs when large pressure is locally applied during molding of a sealing resin layer 122. Therefore, the thickness of the memory chip 109 at the first step can be set in a range of, for example, 40 micrometers to 50 micrometers and the thickness of the other memory chips 109 (at the second to eighth steps) can be set, for example, 10 micrometers to 40 micrometers to suppress an increase in lamination thickness.

The thickness of the memory chips 109 included in the second memory chip group 113 is not always limited either. However, it is desirable to set the thickness of the memory chip 109 at the bottom step (the ninth step) larger than the thickness of the other memory chips (the memory chips at the tenth to sixteenth steps) 109. This is because, although the memory chip 109 at the ninth step is supported by the memory chip 109 at the eight step, a supporting structure for the memory chip 109 at the ninth step is inferior to those for the other memory chips 109. Therefore, the thickness of the memory chip 109 at the ninth step can be set in a range of, for example, 25 micrometers to 40 micrometers and the thickness of the other memory chips 109 (at the tenth to sixteenth steps) can be set in a range of, for example, 10 micrometers to 25 micrometers.

On the second principal plane 102b of the wiring substrate 102 mounted with the memory chips 109 and the controller chip 111 as explained above, the sealing resin layer 122 made of, for example, epoxy resin is molded. The memory chips 109 and the controller chip 111 are integrally sealed by the sealing resin layer 122 together with the metal wires 114, 116, 118A, and 118B. At the leading end (the short side 103A side) of the sealing resin layer 122, an inclining section 123 indicating the front of the semiconductor memory card is provided. At the trailing end (the short side 1033 side) of the sealing resin layer 122, a grip section 124 formed by partially heaping up sealing resin is provided. The semiconductor device 100 used as the semiconductor memory card includes these members.

The semiconductor device 100 alone configures the semiconductor memory card (e.g., a micro SD card) without using a storage case such as a base card. Therefore, the sealing resin layer 122 and the like are directly exposed to the outside. In other words, the semiconductor device 100 is used as a caseless semiconductor memory card from which the sealing resin layer 122 and the like are exposed to the outside. Therefore, the cutout and the narrowed section indicating the directions of the front and the rear and the front side and the back side of the semiconductor memory card and the inclining section 123 are provided in the semiconductor device 100 itself.

In the semiconductor memory card such as the micro SD card, external dimensions of the product are determined. Therefore, to attain a further increase in capacity, it is required to increase the number of steps of memory chips laminated in the semiconductor memory card and reduce the thickness of one chip. In recent years, chips having thickness equal to or smaller than 85 micrometers are laminated. In particular, in a small semiconductor memory card such as the micro SD card, memory chips having thickness equal to or smaller than 20 micrometers are also laminated.

As explained in the background of the invention, when the chip thickness is reduced to 100 micrometers, it is likely that deflective strength falls and the chips are broken during mounting. Therefore, in the case of the chips having thickness equal to or smaller than 100 micrometers, the structure explained in the first embodiment, i.e., the structure in which the rear surfaces of the chips (the wafers) 20 are planarized by the polishing processing to form the rear-surface treatment film 11 formed of the organic film having plus charges on the outer side can be applied.

According to the experiment of the inventors, it was found that, at thickness equal to or larger than 85 micrometers, even if fractured layers were formed on the rear surfaces of the chips 20 by the rear-surface polishing processing using the grindstone #2,000, the chips could be mounted without causing a crack and, up to thickness of 55 micrometers, even if fractured layers were formed on the rear surfaces of the chips 20 by the rear-surface polishing processing using the grindstone #8,000, the chips 20 could be mounted without causing a crack. However, in the case of such thin chips 20, it is necessary to sufficiently clean the chips 20 to prevent ionic impurities from remaining on the apparatus during the rear-surface polishing processing. Therefore, even if the rear surfaces of the chips 20 are not planarized to form the rear-surface treatment films 11 formed of organic films, it is possible to manufacture the chips 20 having thickness equal to or larger than 55 micrometers.

However, when the chips 20 has thickness smaller than 55 micrometers, in some case, the deflective strength falls and the chips 20 are broken when mounted. When the semiconductor memory card using the chips 20 from which the fractured layers on the rear surfaces are removed is manufactured, it is found that, in some case, a deficiency occurred in a data retention characteristic in the semiconductor memory card manufactured in this way. This is considered to be because, since the fractured layers were not formed on the rear surfaces of the chips 20 and the barrier function against ionic impurities was not provided, the ionic impurities were diffused in the semiconductor substrate (the wafer) 10. Although not shown in the figure, in a semiconductor device having a structure in which a plurality of semiconductor chips such as memory chips having rear surfaces planarized without forming the fractured layers were laminated in one package and having a solder ball as an external connection terminal, when heat was applied in reflow processing, in some case, occurrence of a deficiency of the data retention characteristic was found. This is considered to be because the ionic impurities were diffused by the heat applied in the reflow processing. Therefore, it is particularly desirable that a structure in which the rear-surface treatment film 11 formed of the organic film is formed on the rear surface of a chip thinner than 55 micrometers planarized by the rear-surface polishing processing is applied to the chips.

In this case, for example, in the laminated structure shown in FIG. 7, a structure in which the rear surfaces of all the memory chips 109 are subjected to planarization processing and the rear-surface treatment films 11 are formed can be applied. Alternatively, a structure in which only the rear surfaces of arbitrary memory chips 109 are subjected to the planarization processing and the rear-surface treatment films 11 are formed can be applied.

When the structure according to the first embodiment is applied to the arbitrary memory chips 109, for example, presence or absence of arrangement of memory chips, the rear surfaces of which are planarized and on which the rear-surface treatment films 11 having the barrier function are formed, can be changed according to a degree of contamination due to ionic impurities in positions where the memory chips 109 are mounted (laminated). For example, in the case of the structure in which the memory chips 109 are laminated on the wiring substrate 102 shown in FIG. 7, a large number of ionic impurities adhere to the wiring substrate 102. Therefore, a memory chip thicker than 55 micrometers and having a structure in which a fractured layer is formed on the rear surface thereof to have a gettering function and the barrier function against the ionic impurities can be applied to the memory chip 109 at the bottom step. A memory chip thinner than 55 micrometers and having a structure in which an organic film having the barrier function against ionic impurities is formed on the planarized rear surface thereof is applied to the other memory chips 109 and the controller chip 111, more specifically, the upper memory chips 109 and the controller chip 111. However, this is only an example and it can be arbitrarily determined to which semiconductor chip a semiconductor chip having the structure in which the rear-surface treatment film 11 planarized on the rear surface and having the barrier function is formed is applied.

In the above explanation, the micro SD card is explained as the example. However, the present invention can also be applied to, for example, other semiconductor memory cards and a solid state drives (SSD) having a structure in which a plurality of memory chips are laminated, a multi chip package (MCP) having a structure in which a plurality of semiconductor chips are laminated in one semiconductor package.

According to the second embodiment, in the semiconductor device in which a plurality of chips are laminated, the rear surfaces of the chips thinner than 100 micrometers, more desirably, 55 micrometers are planarized and the rear-surface treatment films 11 formed of the organic films including the functional group having plus charges on the outer side are provided on the rear surfaces. Therefore, there is an effect that it is possible to increase the deflective strength and impart the barrier function against ionic impurities to the semiconductor device. In particular, even when heat is applied in the reflow processing or the like and the ionic impurities are activated to easily move, it is possible to prevent the moving ionic impurities from intruding into the semiconductor substrates (chips).

Because the rear-surface treatment film 11 is formed as the self-organizing monomolecular film, the thickness thereof can be reduced to several nanometers and the rear-surface treatment film 11 does not affect the thickness of the chips. Therefore, for example, when the rear-surface treatment film 11 is used for chips used in a semiconductor memory card or the like having specified thickness, there is also an effect that the rear-surface treatment film 11 does not affect the thickness of the chips.

As explained above, according to the embodiments of the present invention, there is an effect that even a semiconductor substrate (a wafer or chips) having thickness not enough for forming a fractured layer, has deflective strength enough for withstanding pressure during mounting of the chips and it is possible to prevent intrusion of ionic impurities from the rear surface of the semiconductor substrate.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A semiconductor chip having devices formed on a first principal plane of a semiconductor substrate, wherein
    a second principal plane of the semiconductor substrate is planarized, and
    an organic film is provided on the second principal plane, the organic film having an outer side with plus charges.

2. The semiconductor chip according to claim 1, further comprising a die attach film provided on the organic film,
    wherein the organic film is a self-organizing monomolecular film.

3. A semiconductor device formed by laminating, on a wiring substrate, a plurality of semiconductor chips, wherein at least one semiconductor chip is the semiconductor chip according to claim 1.

4. The semiconductor device according to claim 3, wherein at least one semiconductor chip among the semiconductor chips is thicker than the other semiconductor chips, and includes not the organic film but a structure in which a fractured layer is formed on the second principal surface of the semiconductor substrate.

5. The semiconductor device according to claim 3, wherein
    the semiconductor chip at a bottom step among the laminated semiconductor chips is thicker than the other semiconductor chips, and includes not the organic film but a structure in which a fractured layer is formed on the second principal plane of the semiconductor substrate, and
    the second principal planes of the semiconductor substrates of the other semiconductor chips are planarized, organic films provided on the second principal planes, and the organic films have an outer side with plus charges.

6. The semiconductor device according to claim 3, wherein the laminated semiconductor chips include:
    a first chip group in which the semiconductor chips are laminated stepwise to be shifted a predetermined distance in a first direction; and
    a second chip group in which the semiconductor chips are laminated stepwise to be shifted a predetermined distance in a second direction opposite to the first direction on the semiconductor chip in a top layer of the first chip group.

7. The semiconductor device according to claim 6, wherein
the semiconductor chip at a bottom step among the semiconductor chips included in each of the first and second chip groups is thicker than the other semiconductor chips, and includes not the organic film but a structure in which a fractured layer is formed on the second principal plane of the semiconductor substrate, and the second principal planes of the semiconductor substrates of the other semiconductor chips are planarized, organic films provided on the second principal planes, and the organic films having an outer side with plus charges.

8. The semiconductor device according to claim 3, wherein deflective strength of the semiconductor chip including the organic film is equal to or larger than 3 N.

9. The semiconductor device according to claim 3, wherein arithmetic mean roughness of the second principal plane of the semiconductor substrate is equal to or smaller than 1 nanometer.

10. The semiconductor device according to claim 3, wherein the organic film is a self-organizing monomolecular film.

11. The semiconductor chip according to claim 1, wherein a thickness of the semiconductor substrate is equal to or smaller than 100 micrometers.

12. The semiconductor chip according to claim 11, wherein an arithmetic mean roughness Ra of the second principal plane of the semiconductor substrate is equal to or smaller than 1 nanometer.

13. The semiconductor chip according to claim 1, wherein the second principal plane of the semiconductor substrate has an oxidized surface to which the organic film is applied.

14. The semiconductor chip according to claim 1, wherein the organic film comprises a silane coupling agent and the silane coupling agent is covalently bonded to an oxidized surface of the second principal plane of the semiconductor substrate.

15. A semiconductor chip, which comprises:
a semiconductor substrate,
a first principal plane arranged on one side of the substrate,
a second principal plane arranged on another side of the substrate opposite the one side of the substrate,
one of the first and second principal planes being a device-side principal plane, the device-side principal plane having devices arranged thereon, and
another of the first and second principal planes being a backside principal plane, the backside principal plane being planarized and coated with an organic film, the organic film having an outer side with plus charges that faces away from the second principal plane, and the organic film together with the semiconductor substrate being configured to prevent intrusion of ionic impurities into the semiconductor substrate and to increase deflective strength of the semiconductor substrate.

16. The semiconductor device according to claim 15, wherein the deflective strength of the semiconductor substrate including the organic film is equal to or larger than 3 N at a semiconductor substrate thickness of 55 micrometers.

17. The semiconductor chip according to claim 15, wherein a thickness of the semiconductor substrate is equal to or smaller than 100 micrometers.

18. The semiconductor chip according to claim 15, wherein an arithmetic mean roughness Ra of the backside principal plane of the semiconductor substrate is equal to or smaller than 1 nanometer at a semiconductor substrate thickness of 55 micrometers.

19. The semiconductor chip according to claim 15, wherein the backside principal plane of the semiconductor substrate has an oxidized surface on which the organic film is applied.

20. The semiconductor chip according to claim 15, wherein the organic film comprises a silane coupling agent and the silane coupling agent is covalently bonded to an oxidized surface of the backside principal plane of the semiconductor substrate.

* * * * *